(12) United States Patent
Kravtchenko et al.

(10) Patent No.: US 7,354,459 B2
(45) Date of Patent: Apr. 8, 2008

(54) USE OF ORGANOSILANE COMPOUNDS FOR DYEING KERATIN FIBERS

(75) Inventors: Sylvain Kravtchenko, Asnieres (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 314 days.

(21) Appl. No.: 11/265,207

(22) Filed: Nov. 3, 2005

(65) Prior Publication Data

US 2006/0112500 A1 Jun. 1, 2006

Related U.S. Application Data

(60) Provisional application No. 60/634,528, filed on Dec. 10, 2004.

(30) Foreign Application Priority Data

Nov. 3, 2004 (FR) .................................. 04 11714

(51) Int. Cl.
*A61K 7/13* (2006.01)
(52) U.S. Cl. ....................... 8/405; 8/406; 8/408; 8/410; 8/411; 8/412; 8/421; 8/426; 8/435; 8/581; 8/632; 132/202; 132/208
(58) Field of Classification Search .............. 8/405, 8/406, 408, 410, 411, 412, 421, 426, 435, 8/581, 632; 132/202, 208
See application file for complete search history.

(56) References Cited

U.S. PATENT DOCUMENTS

| | | | |
|---|---|---|---|
| RE30,199 E | 1/1980 | Rose et al. | |
| 4,403,099 A | 9/1983 | Hirsch et al. | |
| 4,823,985 A | 4/1989 | Grollier et al. | |
| 5,061,289 A | 10/1991 | Clausen et al. | |
| 5,380,340 A | 1/1995 | Neunhoffer et al. | |
| 5,534,267 A | 7/1996 | Neunhoffer et al. | |
| 5,663,366 A | 9/1997 | Neunhoffer et al. | |
| 5,708,151 A | 1/1998 | Möckli | |
| 5,766,576 A | 6/1998 | Löwe et al. | |
| 6,027,537 A * | 2/2000 | Leduc et al. .................. | 8/405 |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,458,167 B1 | 10/2002 | Genet et al. | |
| 6,458,168 B1 | 10/2002 | Lagrange et al. | |
| 6,554,872 B2 | 4/2003 | Genet et al. | |
| 6,645,258 B2 | 11/2003 | Vidal et al. | |
| 6,730,789 B1 | 5/2004 | Birault et al. | |
| 2004/0074016 A1 | 4/2004 | Genet et al. | |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 770 375 | 5/1997 |
| EP | 0 940 404 | 9/1999 |
| FR | 2 421 934 | 11/1979 |
| FR | 2 586 913 | 3/1987 |
| FR | 2 733 749 | 11/1996 |
| FR | 2 786 481 | 6/2000 |
| FR | 2 787 705 | 6/2000 |
| FR | 2 788 433 | 7/2000 |
| FR | 2 801 308 | 5/2001 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 03/029359 | 4/2003 |

OTHER PUBLICATIONS

STIC Search Report dated Jun. 14, 2007.*
English Language DERWENT Abstract of EP 0 770 375, 1997.
English Language DERWENT Abstract of EP 0 940 404, 1999.
English Language DERWENT Abstract of JP 2-19576, 1990.
English Language DERWENT Abstract of JP 5-163124, 1993.
International Search Report mailed Jun. 28, 2005 in FR 0411714 (corresponding to the present application).

* cited by examiner

*Primary Examiner*—Eisa Elhilo
(74) *Attorney, Agent, or Firm*—Finnegan, Henderson, Farabow, Garrett & Dunner LLP

(57) ABSTRACT

Disclosed herein are methods for dyeing keratin fibers, for example human keratin fibers such as hair, comprising applying to the keratin fibers a dye composition comprising, as a direct dye, at least one organosilane compound chosen from compounds of formula (I):

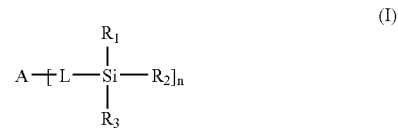

Also disclosed herein are dye compositions for dyeing keratin fibers comprising at least one organosilane compound of formula (I) and at least one oxidation base.

38 Claims, No Drawings

USE OF ORGANOSILANE COMPOUNDS FOR DYEING KERATIN FIBERS

This application claims benefit of U.S. Provisional Application No. 60/634,528, filed Dec. 10, 2004, the contents of which are incorporated herein by reference. This application also claims benefit of priority under 35 U.S.C. § 119 to French Patent Application No. 04 11714, filed Nov. 3, 2004, the contents of which are also incorporated herein by reference.

The present disclosure relates to the use of certain organosilane compounds, for example, compounds comprising at least one trialkoxysilane functional group, as direct dyes in dye compositions for dyeing keratin fibers such as human hair. Also disclosed herein are dye compositions comprising at least one organosilane compound, and the use of these compositions for dyeing keratin fibers.

It is known to dye keratin fibers, for example, human hair, with dye compositions comprising oxidation dye precursors generally called oxidation bases, such as ortho- and para-phenylenediamines, ortho- and para-aminophenols, and heterocyclic compounds. These oxidation bases are colorless or faintly colored compounds which, when combined with oxidizing products, can give rise, through a process of oxidative condensation, to colored compounds. These dyes, which are insoluble in the dyeing medium, are trapped inside the hair.

It is also known that it is possible to vary the shades obtained with these oxidation bases by combining them with couplers or color modifiers, the latter being chosen, for example, from aromatic meta-diamines, meta-aminophenols, meta-diphenols, and certain heterocyclic compounds such as indole compounds.

The variety of molecules used in oxidation bases and couplers allows a rich pallet of colors to be obtained.

The so-called "permanent" color obtained using these oxidation dyes ideally satisfies one or more of a number of requirements. For example, it is expected that oxidation dyes should be without drawbacks from the toxicological point of view, should make it possible to obtain shades in the desired intensity, should exhibit good fastness toward external agents such as light, adverse weather conditions, washing, permanent waving, perspiration, and rubbing, should make it possible to cover grey hair and/or should be as unselective as possible, i.e., make it possible to obtain the smallest possible differences in color along the same keratin fiber, which is in general differently sensitized (i.e. damaged) between its tip and its root.

It is also known to dye keratin fibers by direct or semipermanent dyeing. The method conventionally used in direct dyeing comprises applying to the keratin fibers direct dyes which are colored and coloring molecules having affinity for the fibers, and leaving the dye on the fibers for a time sufficient to allow the colored molecules to penetrate, by diffusion, inside the hair, and then rinsing the fibers.

Unlike the oxidation dye compositions, the direct or semipermanent dye compositions may be used in the presence or in the absence of an oxidizing agent. Direct dyeing typically may be performed repeatedly without damaging the keratin fiber.

It is known, for example, to use nitrobenzene, anthraquinone, nitropyridine, azo, xanthene, acridine, azine, and triarylmethane direct dyes.

The result is particularly chromatic colors which are nevertheless temporary or semipermanent because of the nature of the bonds between the direct dyes and the keratin fiber. These interactions are such that the desorption of the dyes from the surface and/or from the core of the fiber occurs easily. The colors generally exhibit a weak color intensity and a poor fastness to washing and/or perspiration. In addition, these direct dyes are generally sensitive to light because the resistance of the chromophore to photochemical attacks is low, which leads to fading of the color of the hair over time. The sensitivity of these dyes to light depends on their uniform distribution or their distribution in the form of aggregates in and/or on the keratin fiber.

Moreover, conventional direct dyes may not be completely harmless, thus, in hair cosmetics, dye molecules of this type are being sought with ever greater performance in terms of safety. In addition, it is very much desirable to provide improved direct dye compositions in terms of fastness to shampoos and rinsing of the dye.

The present inventors have surprisingly discovered that the use of particular organosilane compounds in compositions for dyeing keratin fibers, for example, human keratin fibers such as hair, make it possible to obtain dye compositions which exhibit the above-mentioned improvements.

In addition to their advantage in terms of safety, the compositions according to the present disclosure may make it possible to obtain colors which are resistant to external agents (such as sunlight and adverse weather conditions), shampoos, and/or perspiration, and/or make it possible to obtain intense and fast glints on the fibers. The compositions may also exhibit improved rinsing and/or good toxicological profiles.

Thus, disclosed herein is a method for direct dyeing of keratin fibers, such as human hair, by applying to the fibers a dye composition comprising at least one particular type of organosilane compound.

Also disclosed herein is a dye composition for dyeing keratin fibers, e.g., human keratin fibers such as hair, comprising, in an appropriate dye medium, at least one oxidation base and at least one particular type of organosilane compound.

Further disclosed herein is a method for dyeing keratin fibers, for example, human keratin fibers such as hair, comprising applying to the keratin fibers a dye composition comprising at least one particular type of organosilane compound and at least one oxidation base.

In at least one embodiment, the method may comprise applying to the keratin fibers a first composition according to the present disclosure, and then applying to the keratin fibers, after an optional rinse, a second composition containing an alkaline agent.

Further disclosed herein is a method for providing keratin fibers, for example human keratin fibers such as hair, with a color exhibiting good resistance to external agents and shampoos, comprising applying a dye composition comprising at least one organosilane compound to the keratin fibers.

Other characteristics, aspects, subjects, and advantages of the present disclosure will emerge even more clearly on reading the description and the examples which follow.

Organosilane Compounds

Sutiable organosilane compounds in accordance with the present disclosure may be chosen from compounds of formula (I):

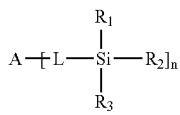

(I)

in which:
A is a group having a direct dyeing function,
L is a linking arm,
$R_1$, $R_2$, and $R_3$, independently of each other, are chosen from hydrogen; mono- and polyhydroxyalkyl radicals comprising from 1 to 10 carbon atoms; mono- and polyaminoalkyl radicals comprising from 1 to 10 carbon atoms; mono- and polyhaloalkyl radicals comprising from 1 to 10 carbon atoms; mono- and polyalkoxyalkyl radicals, wherein the alkoxy radical is chosen from $C_1$-$C_{10}$ alkoxy radicals and the alkyl radical is chosen from $C_1$-$C_{10}$ alkyl radicals; $C_6$-$C_{18}$ aryl radicals; $C_6$-$C_{18}$ mono- and polyaminoaryl radical; $C_6$-$C_{18}$ mono- and polyhydroxyaryl radicals; mono- and polyalkoxyaryl radicals, wherein the alkoxy radical is chosen from $C_1$-$C_{10}$ alkoxy radicals and the aryl radical is chosen from $C_6$-$C_{18}$ aryl radicals; alkylaryl radicals, wherein the alkyl radical is chosen from $C_1$-$C_{10}$ alkyl radicals and the aryl radical is chosen from $C_6$-$C_{18}$ radicals; arylalkyl radicals, wherein the alkyl radical is chosen from $C_1$-$C_{10}$ alkyl radicals and the aryl radical is chosen from $C_6$-$C_{18}$c aryl radicals; and carboxyalkyl and sulphoalkyl radicals, wherein the alkyl radical is chosen from $C_1$-$C_{10}$ alkyl radicals, and
n is an integer ranging from 1 to 10.

According to one embodiment of the present disclosure, the alkyl radicals of $R_1$, $R_2$, and $R_3$ may be chosen from $C_1$-$C_6$ alkyl radicals.

In at least one embodiment, the organosilane compounds may be chosen from compounds comprising at least one trialkoxysilane functional group, for example, compounds corresponding to formula (II):

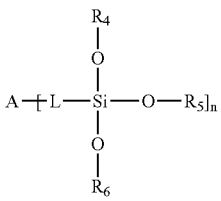

(II)

in which:
A is a group having a direct dyeing function,
L is a linking arm,
$R_4$, $R_5$, and $R_6$, independently of each other, are chosen from substituted or unsubstituted, linear or branched, $C_1$-$C_{10}$, for example, $C_1$-$C_6$, alkyl radicals, and
n is an integer ranging from 1 to 10.

In one embodiment, the alkyl radical corresponding to $R_4$, $R_5$, and $R_6$ may be chosen from methyl, ethyl, n-propyl, isopropyl, and butyl radicals. In another embodiment, this alkyl radical may be chosen from methyl and ethyl radicals.

The group A is a group having a direct dyeing function. As used herein, the expression "group having a direct dyeing function" is understood to mean a group exhibiting an absorption ranging from 350 to 800 nm.

The group A may be chosen from, for example, radicals derived from aromatic nitro, anthraquinone, naphthoquinone, benzoquinone, azo, xanthene, triarylmethane, azine, thiazine, phenothiazine, diazine, phenodiazine, acridine, cyaninemethine, azomethine, nitro, phthalocyanine, indoaniline, indophenole, and indoamine dyes, and natural direct dyes.

Examples of benzene direct dyes which make it possible to generate the group A according to the present disclosure, include but are not limited to, the following compounds:
1,4-diamino-2-nitrobenzene,
1-amino-2-nitro-4-β-hydroxyethylaminobenzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis-(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis-(β-hydroxyethylamino)-4-nitrobenzene,
1-amino-2-tris-(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis-(β-hydroxyethyl)amino-3-nitrobenzene,
1-β-hydroxyethylamino-2-nitrobenzene, and
1-hydroxy-4-β-hydroxyethylamino-3-nitrobenzene.

Non-limiting examples of azo direct dyes which make it possible to generate the group A according to the present disclosure, include the cationic azo dyes described in International Publication Nos. WO 95/15144 and WO 95/01772 and European Patent No. 0 714 954, which are incorporated herein by reference. For example, the azo direct dyes may be chosen from:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulphate Suitable azo direct dyes may also include the following dyes, which are described in the Colour Index International $3^{rd}$ edition:
Disperse Red 17,
Acid Yellow 9, Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24, and
Disperse Black 9.

Further examples of suitable azo direct dyes include, but are not limited to, 1-(4'-aminodiphenylazo)-2-methyl-4bis-(β-hydroxyethyl)aminobenzene and 4-hydroxy-3-(2-methoxyphenylazo)-1-naphthalenesulphonic acid.

Non-limiting examples of quinone direct dyes include:
Disperse Red 15,
Solvent Violet 13,
Acid Violet 43,
Disperse Violet 1,
Disperse Violet 4,
Disperse Blue 1,
Disperse Violet 8,
Disperse Blue 3,
Disperse Red 11,
Acid Blue 62,
Disperse Blue 7,
Basic Blue 22,
Disperse Violet 15,
Basic Blue 99,
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone, and
1,4-Bis-(β,γ-dihydroxypropylamino)anthraquinone.

Suitable azine dyes include, for example, Basic Blue 17 and Basic Red 2.

Examples of triarylmethane dyes which may be used in accordance with the present disclosure include, but are not limited to:
Basic Green 1,
Acid blue 9,
Basic Violet 3,
Basic Violet 14,
Basic Blue 7,
Acid Violet 49,
Basic Blue 26, and
Acid Blue 7.

Non-limiting examples of indoamine dyes which may be used according to the present disclosure include:
2-β-hydroxyethlyamino-5-[bis-(β-4'-hydroxyethyl)amino] anilino-1,4-benzoquinone,
2-β-hydroxyethylamino-5-(2'-methoxy-4'-amino)anilino-1,4-benzoquinone,
3-N(2'-chloro-4'-hydroxy)phenylacetylamino-6-methoxy-1,4-benzoquinone imine,
3-N(3'-chloro-4'-methylamino)phenylureido-6-methyl-1,4-benzoquinone imine, and
3-[4'-N-(ethylcarbamylmethyl)amino]phenylureido-6-methyl-1,4-benzoquinone imine.

Suitable natural direct dyes which make it possible to generate the group A according to the present disclosure include, for example, lawsone, juglone, alizarin, purpurin, carminic acid, kermesic acid, purpurogallin, protocatechaldehyde, indigo, isatin, curcumin, spinulosin, and apigenidin.

The group L represents a "linking arm." As used herein, the expression "linking arm" is understood to mean an atom or a group of atoms separating the chromophore group from the at least one alkoxysilane group. It may be a hydrocarbon chain which may be substituted or interrupted by a heteroatom such as O, N, and Si; or by a ring chosen from substituted or unsubstituted aromatic and heteroaromatic rings.

The linking arm may be cationic or noncationic.

The linking arm may be chosen, for example, from linear or branched, $C_1$-$C_{20}$, for example, $C_1$-$C_6$, hydrocarbon chains, it being possible for at least one of the carbon atoms of the chain to be replaced by a heteroatom such as sulphur, nitrogen, and oxygen, it being possible for the hydrocarbon chain to be saturated or unsaturated, or to comprise at least one radical chosen from arylene radicals; divalent terephthalamide radicals; divalent triazine radicals; and —NH—CO— radicals.

The hydrocarbon chain may be substituted, for example, with at least one radical chosen from hydroxy, alkoxy, amino, alkylamino, and halogen radicals.

Non-limiting examples of linking arms include, but are not limited to, alkylene ($C_nH_{2n}$) radicals, comprising, for example, from 1 to 6 carbon atoms, such as methylene, ethylene, propylene, and the like; (hetero)arylene radicals, for example, phenylene, naphthalene, phenanthrylene, triazinyl, pyrimidinyl, pyridinyl, pyridazinyl, quinoxalinyl, and alkyl-aryl-alkyl radicals.

Further examples of suitable linking arms include, but are not limited to, the triazines described in International Publication No. WO 03/029359, the alkylenes mentioned in U.S. Pat. No. 5,708,151, and the alkyl-aryl-alkyl radicals mentioned in U.S. Pat. No. 5,708,151.

In one embodiment, the linking arm L may be chosen from linear or branched $C_1$-$C_{20}$, for example, $C_1$-$C_6$, alkylene chains.

As used herein, in the context of the definitions of the groups $R_4$, $R_5$, and $R_6$, the expression "substituted" is understood to mean substituted with at least one group chosen from hydroxyl; halogen; linear or branched $C_1$-$C_6$ alkoxy; amino; acetylamino; linear or branched $C_1$-$C_6$ alkylcarbonyl; hydroxycarbonyl; and linear or branched $C_1$-$C_6$ alkoxycarbonyl groups.

In at least one embodiment, the compounds of formula (I) and (II) may be chosen from:
benzenesulphonate of 4-amino-5-[[4'-[(4-hydroxyphenyl)azo]-3,3'-dimethyl[1,1'-biphenyl]-4-yl]azo]-2-[[2-hydroxy-3-[3-(trimethoxysilyl)propoxy]propyl]amino],
benzoate of 4-[(4-ethoxyphenyl)azo]-, 3-(triethoxysilyl)propyl ester,
benzoate of 4-[(4-ethoxyphenyl)azo]-, 2-(triethoxysilyl) ethyl ester,
acetamide, N-[2-[[4-amino-6-[(3,3,4,4,5,5,6,6,7,7,8,8,9,9,10,10,10-hexadecafluorodecyl)oxy]-1,3,5-triazin-2-yl]amino]-5-[[4,8-bis[[[3-(trimethoxysilyl)propyl]amino]sulphonyl]-2-naphthalenyl]azo]phenyl],
acetamide, N-[2-[[4-amino-6-[(3,3,4,4,5,5,6,6,7,7,8,8,9,9,10,10,10-heptadecafluorodecyl)oxy]-1,3,5-triazin-2-yl]amino]-5-[[4,8-bis[[[3-(trimethoxysilyl)propyl]amino]sulphonyl]-2-naphthalenyl]azo]phenyl],
acetamide, N-[2-[[4-amino-6-(2,2-difluoro-2-hydroxyethoxy)-1,3,5-triazin-2-yl]amino]-5-[[4,8-bis[[[3-(trimethoxysilyl)propyl]amino]sulphonyl]-2-naphthalenyl]azo]phenyl], acetamide, N-[2-[[4-amino-6-(2,2-difluoro-2-hydroxyethoxy)-1,3,5-triazin-2-yl]amino]-5-[[4,8-bis[[[3-(triethoxysilyl)propyl]amino]sulphonyl]-2-naphthalenyl]azo]phenyl], N-[4-[(1E)-phenylazo]phenyl]-N'-[3-(triethoxysilyl)propyl] urea, carbamate of [3-(triethoxysilyl)propyl]-, 2-[ethyl[4-[(4-nitrophenyl)azo]phenyl]amino]ethyl ester, carbamate of [3-(trimethoxysilyl)propyl]-, [[4-[(4-nitrophenyl)azo]phenyl]imino]di-2,1-ethanediyl ester, carbamate of [3-(trimethoxysilyl)propyl]-, 2-[ethyl[4-[(4-nitrophenyl)azo]phenyl]amino]ethyl 2,7-naphthalenedisulphonate of 4-amino-3-[[4-[[2-amino-4-[[[[3-(triethoxysilyl)propyl]amino]carbonyl]oxy]phenyl]azo]phenyl]amino]-3-sulphophenyl]azo]-5-hydroxy-6-(phenylazo), benzamide, 2-[(1E)-[4-(dimethylamino)phenyl]azo]-N-[3-(triethoxysilyl)propyl, carbamate of [3-(triethoxysilyl)propyl]-, [[4-[(4-nitrophenyl)azo]phenyl]imino]di-2,1-ethanediyl ester, 2-[ethyl[4-[(1E)-(4-nitrophenyl)azo]phenyl]amino]ethyl [3-(triethoxysilyl)propyl]carbamate, benzonitrile, 4-[[4-[bis[2-[3-(trimethoxysilyl)propoxy]ethyl]amino]phenyl]azo]-, benzenesulphonamide, 4-(2-benzothiazolylazo)-N-[3-(trimethoxysilyl)propyl], 2-propanol, 1,1'-[[[4-[(4-nitrophenyl)azo]phenyl]imino]bis(4,1-phenyleneimino)]bis[3-[3-(trimethoxysilyl)propoxy, urea, N,N''-[(1Z)-azodi-4,1-phenylene]bis[N'-[3-(triethoxysilyl)propyl], urea, N,N''-[(1E)-azodi-4,1-phenylene]bis[N'-[3-(triethoxysilyl)propyl], iodide pyridinium, 4-[6-[[4-[bis[2-[[(1,1-dimethylethyl)dimethylsilyl]oxy]ethyl]amino]phenyl]azo]-2-benzothiazolyl]-1-[3-(trimethoxysilyl)propyl], 2-propenoate, 2-methyl-, 2-[ethyl[4-[(4-nitrophenyl)azo]phenyl]amino]ethyl ester, carbamate of [3-(triethoxysilyl)propyl]-, 4-[(4-nitrophenyl)azo]phenyl ester, carbamate of [3-(triethoxysilyl)propyl]-, [[4-[[4-[(13,13-diethoxy-8-oxo-7,14-dioxa-9-aza-13-silahexadec-1-yl)sulphonyl]phenyl]azo]phenyl]imino]di-2,1-ethanediyl ester, carbamate of [3-(triethoxysilyl)propyl]-, 6-[[4-[[4-[(9,9-diethoxy-4-oxo-3,10-dioxa-5-aza-9-siladodec-1-yl)methylamino]phenyl]azo]phenyl]sulphonyl]hexyl ester, carbamate of [3-(triethoxysilyl)propyl]-, [[4-[[4-(butylsulphonyl)phenyl]azo]phenyl]imino]di-2,1-ethanediyl ester, urea, N-[4-(phenylazo)phenyl]-N'-[3-(triethoxysilyl)propyl 1-[[4-[(4-nitrophenyl)azo]phenyl]amino]-3-[3-(trimethoxysilyl)propoxy]-2-propanol, carbamate of [3-(triethoxysilyl)propyl]-, 2-[2,5-dimethyl-4-[(4-nitrophenyl)azo]phenoxy]ethyl ester, pyridinium, 4-[[4-[bis[2-[[(1,1-dimethylethyl)dimethylsilyl]oxy]ethyl]amino]phenyl]azo]-1-[3-(trimethoxysilyl)], 2,7-naphthalenedicarboxamide, 3-hydroxy-4-[[2-methoxy-5-[(phenylamino)carbonyl]phenyl]azo]-N-2-1-naphthalenyl-N-7-[2-[[3-(trimethoxysilyl)propyl]amino]ethyl], 2,7-naphthalenedicarboxamide, 3-hydroxy-4-[[2-methoxy-5-[(phenylamino)carbonyl]phenyl]azo]-N-2-1-naphthalenyl-N-7-[3-(triethoxysilyl)propyl], 1H-pyrazole-3-carboxamide, 4,5-dihydro-5-oxo-1-phenyl-4-(phenylazo)-N-[3-(trimethoxysilyl)propyl, benzamide, 4-[[4-(dimethylamino)phenyl]azo]-N-[3-(triethoxysilyl)propyl], benzamide, 4-(phenylazo)-N-[3-(triethoxysilyl)propyl], benzamide, 2-[[4-(dimethylamino)phenyl]azo]-N-[3-(trimethoxysilyl)propyl], carbamate of [3-(triethoxysilyl)propyl]-, [[4-[(1E)-(4-nitrophenyl)azo]phenyl]imino]di-2,1-ethanediyl ester, carbamate of [3-(triethoxysilyl)propyl]-, [[4-[[4-[[[3-(triethoxysilyl)propyl]amino]carbonyl]amino]phenyl]sulphonyl]phenyl]azo]phenyl]imino]di-2,1-ethanediyl ester, 1H-isoindole-5-carboxylic acid, 2,3-dihydro-1,3-dioxo-2-[3-(triethoxysilyl)propyl]-, 5-(diethylamino)-2-[[2-[[[2,3-dihydro-1,3-dioxo-2-[3-(triethoxysilyl)propyl]-1H-isoindol-5-yl]carbonyl]oxy]-4-nitrophenyl]azo]phenyl ester, carbamate of [3-(triethoxysilyl)propyl]-, [[4-[[2-[(9,9-diethoxy-4-oxo-3,10-dioxa-5-aza-9-siladodec-1-yl)oxy]-4-nitrophenyl]azo]phenyl]imino]di-2,1-ethanediyl ester, carbamate of [3-(triethoxysilyl)propyl]-, 2-[2-[[2-[(9,9-diethoxy-4-oxo-3,10-dioxa-5-aza-9-siladodec-1-yl)oxy]-4-(diethylamino)phenyl]azo]-5-nitrophenoxy]ethyl ester, carbamate of [3-(triethoxysilyl)propyl]-, [ethyl[4-[(4-nitrophenyl)azo]phenyl]amino]methyl ester, undecanamide, 11-[4-[(4-methylphenyl)azo]phenoxy]-N-[3-(triethoxysilyl)propyl]-, acetamide, N-[2-[[4,5-dicyano-1-[3-(trimethoxysilyl)propyl]-1H-imidazol-2-yl]azo]-5-(diethylamino)phenyl], benzamide, 4-[(5-cyano-1,6-dihydro-2-hydroxy-1,4-dimethyl-6-oxo-3-pyridinyl)azo]-N-[3-(trimethoxysilyl)propyl, carbamate of [3-(triethoxysilyl)propyl]-, 6-[methyl[4-[(4-nitrophenyl)azo]phenyl]amino]hexyl ester, undecanamide, 11-[4-[(4-pentylphenyl)azo]phenoxy]-N-[11-(triethoxysilyl)undecyl], hexanamide, 6-4-[(4-pentylphenyl)azo]phenoxy]-N-[11-(triethoxysilyl)undecyl], propanamide, 3-4-[(4-pentylphenyl)azo]phenoxy]-N-[11-(triethoxysilyl)undecyl, undecanamide, 11-[4-(phenylazo)phenoxy]-N-[11-(triethoxysilyl)undecyl], hexanamide, 6-[4-(phenylazo)phenoxy]-N-[11-(triethoxysilyl)undecyl], propanamide, 3-[4-(phenylazo)phenoxy]-N-[11-(triethoxysilyl)undecyl], propanamide, 3-[4-[(4-pentylphenyl)azo]phenoxy]-N-[3-(triethoxysilyl)propyl], undecanamide, 11-[4-(phenylazo)phenoxy]-N-[3-(triethoxysilyl)propyl], propanamide, 3-[4-(phenylazo)phenoxy]-N-[3-(triethoxysilyl)propyl, hexanamide, 6-[4-[(4-pentylphenyl)azo]phenoxy]-N-[3-(triethoxysilyl)propyl]-, carbamate of [3-(triethoxysilyl)propyl]-, [[3-methyl-4-[(4-nitrophenyl)azo]phenyl]imino]di-2,1-ethanediyl ester, hexanamide, 6-[5-[(4-cyanophenyl)azo]-2-(hexyloxy)phenoxy]-N-[3-(triethoxysilyl)propyl]-, hexanamide, 6-[2-[(4-cyanophenyl)azo]-5-(hexyloxy)phenoxy]-N-[3-(triethoxysilyl)propyl, acetamide, 2-[5-(hexyloxy)-2-[(4-hexylphenyl)azo]phenoxy]-N-[3-(triethoxysilyl)propyl]-, hexanamide, 6-[5-(hexyloxy)-2-[(4-hexylphenyl)azo]phenoxy]-N-[3-(triethoxysilyl)propyl]-, hexanamide, 6-[4-[(4-cyanophenyl)azo]phenoxy]-N-[3-(triethoxysilyl)propyl], undecanamide, 11-[4-[(4-pentylphenyl)azo]phenoxy]-N-[3-(triethoxysilyl)propyl], hexanamide, 6-[4-[(4-pentylphenyl)azo]phenoxy]-N-[3-(triethoxysilyl)propyl], benzamide, 3-[β-hydroxy-4-(2-pyridinylazo)-2-naphthalenyl]azo]-N-[3-(triethoxysilyl)propyl], benzamide, 4-[(4-methoxyphenyl)azo]-N-[3-(triethoxysilyl)propyl]-, hexanamide, 6-[4-(phenylazo)phenoxy]-N-[3-(triethoxysilyl)propyl]-,
benzamide, 4-[[4-(hexyloxy)phenyl]azo]-N-[3-(triethoxysilyl)propyl]-,
carbamate of [3-(triethoxysilyl)propyl]-, [[3-chloro-4-[(4-nitrophenyl)azo]phenyl]imino]di-2,1-ethanediyl ester,
carbamate of [3-(triethoxysilyl)propyl]-, [[4-[(2,6-dichloro-4-nitrophenyl)azo]phenyl]imino]di-2,1-ethanediyl ester,
carbamate of [3-(triethoxysilyl)propyl]-, [[4-[[4-[(9,9-diethoxy-4-oxo-3,10-dioxa-5-aza-9-siladodec-1-yl)sulphonyl]phenyl]azo]phenyl]imino]di-2,1-ethanediyl ester,
carbamate of [3-(triethoxysilyl)propyl]-, 2-methyl-4-[[4-(phenylazo)phenyl]azo]phenyl ester,
carbamate of [3-(triethoxysilyl)propyl]-, 2-[[4-[(2-chloro-4-nitrophenyl)azo]phenyl]ethylamino]ethyl ester,
carbamate of [3-(triethoxysilyl)propyl]-, 4-[(4-nitrophenyl)azo]-1,3-phenylene ester,
hexanamide, 6-[4-[(4-hexylphenyl)azo]phenoxy]-N-[3-(triethoxysilyl)propyl]-,
2,7-naphthalenedisulphonic acid, 4-hydroxy-5-[[4-[(3-sulphophenyl)amino]-6-[[2-[3-(triethoxysilyl)propoxy]ethyl]amino]-1,3,5-triazin-2-yl]amino]-3-[[4-[[2-[3-(triethoxysilyl)propoxy]ethyl]amino]ethyl]sulphonyl]phenyl]azo],
urea, N-[4-[(4-nitrophenyl)azo]phenyl]-N'-[3-(triethoxysilyl)propyl]-,
benzoate of 2-[[4-(dimethylamino)phenyl]azo]-, 3-(triethoxysilyl)propyl ester,
acetamide, N-[3-(triethoxysilyl)propyl]-2-[4-[[4-[[[3-(triethoxysilyl)propyl]amino]methoxy]phenyl]azo]phenoxy,
alanine, N-[3-(triethoxysilyl)propyl]-, 4-[(4-methoxyphenyl)azo]phenyl ester,
acetamide, 2-[4-[(4-methoxyphenyl)azo]phenoxy]-N-[3-(triethoxysilyl)propyl],
diazene, (4-nitrophenyl)[4-[3-(trimethoxysilyl)propoxy]phenyl],
hexanamide, 6-[4-[(4-ethylphenyl)azo]phenoxy]-N-[3-(triethoxysilyl)propyl,
undecanamide, 11-[5-(hexyloxy)-2-[(4-hexylphenyl)azo]phenoxy]-N-[3-(triethoxysilyl)propyl],
cyclohexanecarboxamide, 4-[4-[[4-(pentyloxy)phenyl]azo]phenyl]-N-[3-(triethoxysilyl)propyl],
benzeneheptanamide, 4-[[4-(pentyloxy)phenyl]azo]-N-[3-(triethoxysilyl)propyl],
hexanamide, 6-[4-[(4-cyanophenyl)azo]phenoxy]-N-[3-(triethoxysilyl)propyl],
acetamide, 2-[4-[(4-hexylphenyl)azo]phenoxy]-N-[3-(triethoxysilyl)propyl,
propanamide, 3-[4-[(4-hexylphenyl)azo]phenoxy]-N-[3-(triethoxysilyl)propyl],
butanamide, 4-[4-[(4-hexylphenyl)azo]phenoxy]-N-[3-(triethoxysilyl)propyl],
benzamide, 4-[[4-(hexyloxy)phenyl]azo]-N-[3-(triethoxysilyl)propyl,
benzamide, 4-[(4-methoxyphenyl)azo]-N-[3-(triethoxysilyl)propyl],
hexanamide, 6-[4-(phenylazo)phenoxy]-N-[3-(triethoxysilyl)propyl],
hexanamide, 6-[4-[(4-chlorophenyl)azo]phenoxy]-N-[3-(triethoxysilyl)propyl],
hexanamide, 6-[4-[(4-cyclohexylphenyl)azo]phenoxy]-N-[3-(triethoxysilyl)propyl,
benzamide, 4-[(8-hydroxy-5-quinolinyl)azo]-N-[3-(triethoxysilyl)propyl,
benzensulphonate of 4-amino-5-[[4'-[(4-hydroxyphenyl)azo]-3,3'-dimethyl[1,1'-biphenyl]-4-yl]azo]-2-[[2-hydroxy-3-[3-(trimethoxysilyl)propoxy]propyl]amino]-, monosodium salt,
phenol, 5-[[4-chloro-6-[[3-(triethoxysilyl)propyl]amino]-1,3,5-triazin-2-yl]oxy]-2-[(2-hydroxyphenyl)azo,
1,3-naphthalenedisulphonic acid, 6-[[4-[[2-hydroxy-3-[3-(triethoxysilyl)propoxy]propyl]amino]phenyl]azo],
1,3-naphthalenedisulphonic acid, 6-[[4-[[4-[[2-hydroxy-3-[3-(triethoxysilyl)propoxy]propyl]amino]phenyl]azo]-1-naphthalenyl]azo],
benzoate of 2-[[2-hydroxy-3-[3-(triethoxysilyl)propoxy]propyl]amino]-5-[(4-nitrophenyl)azo],
2-propanol, 1-[[4-[(4-methyl-2-nitrophenyl)azo]phenyl]amino]-3-[3-(triethoxysilyl)propoxy],
2-propanol, 1-[[4-[(2-chlorophenyl)azo]phenyl]amino]-3-[3-(triethoxysilyl)propoxy],
2-propanol, 1-[[4-[(2-methylphenyl)azo]phenyl]amino]-3-[3-(triethoxysilyl)propoxy],
2-propanol, 1-[[4-[(4-nitrophenyl)azo]phenyl]amino]-3-[3-(triethoxysilyl)propoxy],
carbamate of [3-(trimethoxysilyl)propyl]-, 4-[(4-nitrophenyl)azo]phenyl ester,
carbamate of [3-(trimethoxysilyl)propyl]-, 4-(phenylazo)-1-naphthalenyl ester,
carbamate of [3-(trimethoxysilyl)propyl]-, 4-(phenylazo)phenyl ester,
urea, N-[4-(phenylazo)phenyl]-N'-[3-(trimethoxysilyl)propyl],
urea, N-[4-[[4-(dimethylamino)phenyl]azo]phenyl]-N'-[3-(trimethoxysilyl)propyl],
2-propanol, 1-[[4-(phenylazo)phenyl]amino]-3-[3-(trimethoxysilyl)propoxy],
2-propanol, 1-[[4-(phenylazo)phenyl]amino]-3-[3-(triethoxysilyl)propoxy],
2-propanol, 1-[[4-[(2,4-dinitrophenyl)azo]phenyl]amino]-3-[3-(triethoxysilyl)propoxy],
2,7-naphthalenedisulphonic acid, 4-hydroxy-5-[[p-[methyl[3-(triethoxysilyl)propyl]amino]phenyl]azo],
1,3,6-naphthalenetrisulphonic acid, 8-[[p-[methyl[3-(triethoxysilyl)propyl]amino]phenyl]azo],
s-triazine, 2-chloro-4-[4-(p-tolylazo)-o-toluidino]-6-[[3-(triethoxysilyl)propyl]amino],
2-naphthol, 1-[[p-[2-(triethoxysilyl)ethyl]phenyl]azo],
benzenesulphonate of p-[[p-[methyl[3-(triethoxysilyl)propyl]amino]phenyl]azo,
1,3-naphthalenedisulphonic acid, 7-[[p-[methyl[3-(triethoxysilyl)propyl]amino]phenyl]azo],
s-triazine, 2-anilino-4-(4-p-tolylazo-o-toluidino)-6-[[3-(triethoxysilyl)propyl]amino],
benzoate of p-[[p-[methyl[3-(triethoxysilyl)propyl]amino]phenyl]azo],
benzoate of o-[[p-[methyl[3-(triethoxysilyl)propyl]amino]phenyl]azo],
aniline, N-methyl-p-[(p-nitrophenyl)azo]-N-[3-(triethoxysilyl)propyl], and
aniline, N-methyl-p-(phenylazo)-N-[3-(triethoxysilyl)propyl].

The compounds of formula (I) and (II) may also be chosen from:
xanthylium, 3,6-bis(diethylamino)-9-[2-(ethoxycarbonyl)-4-[[[3-(triethoxysilyl)propyl]amino]sulphonyl]phenyl]-,
benzo[a]phenoxazin-7-ium, 9-(dimethylamino)-2-hydroxy-5-[[3-(triethoxysilyl)propyl]amino]-, 1H,5H,11H,15H-xantheno[2,3,4-ij:5,6,7-i'j']diquinolizin-18-ium, 9-[2-(ethoxycarbonyl)-4-[[[3-(triethoxysilyl)propyl]amino]sulphonyl]phenyl]-2,3,6,7,12,13,16,17-octahydro, pyrano[3,2-g:5,6-g']diquinolin-13-ium, 6-(2-carboxy-3,4,5,6-tetrachlorophenyl)-1-ethyl-1,2,10,11-tetrahydro-2,2,4,8,10,10-hexamethyl-11-[4-oxo-4-[[3-(triethoxysilyl)propyl]amino]butyl], chloride of 1H,5H,11H,15H-xantheno[2,3,4-ij:5,6,7-i'j']diquinolizin-18-ium, 9-[2-(ethoxycarbonyl)-4-[[[3-(triethoxysilyl)propyl]amino]sulphonyl]phenyl]-2,3,6,7,12,13,16,17-octahydro-, chloride of xanthylium, 3,6-bis(diethylamino)-9-[2-(ethoxycarbonyl)-4-[[[3-(triethoxysilyl)propyl]amino]sulphonyl]phenyl], inner salt of 1H,5H,11H,15H-xantheno[2,3,4-ij:5,6,7-i'j']diquinolizin-18-ium, 9-[2-carboxy-4-[[[3-(triethoxysilyl)propyl]amino]sulphonyl]phenyl]-2,3,6,7,12,13,16,17-octahydro, inner salt of xanthylium, 9-[2-carboxy-4-[[[3-(triethoxysilyl)propyl]amino]sulphonyl]phenyl]-3,6-bis(diethylamino), inner salt of 1H,5H,11H,15H-xantheno[2,3,4-ij:5,6,7-i'j']diquinolizin-18-ium, 2,3,6,7,12,13,16,17-octahydro-9-[2-sulpho-4-[[[3-(triethoxysilyl)propyl]amino]sulphonyl]phenyl], inner salt of xanthylium, 3,6-bis(diethylamino)-9-[2-sulpho-4-[[[3-(triethoxysilyl)propyl]amino]sulphonyl]phenyl], bromide of phenothiazin-5-ium, 3,7-bis[bis[3-(trimethoxysilyl)propyl]amino]-, bromide, benzo[a]phenoxazin-7-ium, 9-(dimethylamino)-5-[[3-(triethoxysilyl)propyl]amino]-, chloride of benzo[a]phenoxazin-7-ium, 9-(dimethylamino)-2-hydroxy-5-[[3-(triethoxysilyl)propyl]amino], chloride of benzo[a]phenoxazin-7-ium, 9-(dimethylamino)-5-[[3-(triethoxysilyl)propyl]amino], and inner salt of xanthylium, 3,6-bis(diethylamino)-9-[2-sulpho-4-[[[3-(diethoxymethylsilyl)propyl]amino]sulphonyl]phenyl].

The compounds of formula (I) and (II) may also be chosen from:

2-naphthalenecarboxamide, 4-[[4-(diethylamino)-2-methylphenyl]imino]-1,4-dihydro-1-oxo-N-[3-(trimethoxysilyl)propyl], carbamate of [3-(triethoxysilyl)propyl]-, 2-[[4-[[5-(acetylamino)-2-methyl-4-oxo-2,5-cyclohexadien-1-ylidene]amino]-3-methylphenyl]ethylamino]ethyl ester 2-naphthalenecarbonitrile, 8-amino-5-[(4-heptylphenyl)amino]-1,4-dihydro-1,4-dioxo-3-[[3-(triethoxysilyl)propyl]amino], 1H-naphth[2,3-f]isoindole-1,3,5,10(2H)-tetrone, 4,11-diamino-2-[3-(diethoxymethylsilyl)propyl]-, 1H-pyrrole-2,5-dione, 1-[3-(diethoxymethylsilyl)propyl]-3-[4-(dimethylamino)phenyl]-4-[(4-methylphenyl)sulphonyl]-, 1H-pyrrole-2,5-dione, 3-[4-(dimethylamino)phenyl]-4-[(4-methylphenyl)sulphonyl]-1-[3-(triethoxysilyl)propyl]-, 2-naphthalenecarbonitrile, 8-amino-5-[[4-(dimethylamino)phenyl]amino]-1,4-dihydro-1,4-dioxo-3-[[3-(triethoxysilyl)propyl]amino]-, 2-naphthalenecarbonitrile, 8-amino-1,4-dihydro-5-[(4-methoxyphenyl)amino]-1,4-dioxo-3-[[3-(triethoxysilyl)propyl]amino]-, 2-naphthalenecarbonitrile, 8-amino-1,4-dihydro-5-[(4-methylphenyl)amino]-1,4-dioxo-3-[[3-(triethoxysilyl)propyl]amino]-, 2-naphthalenecarbonitrile, 8-amino-5-[(4-chlorophenyl)amino]-1,4-dihydro-1,4-dioxo-3-[[3-(triethoxysilyl)propyl]amino]-, 2-naphthalenecarbonitrile, 8-amino-3-[[3-(diethoxymethylsilyl)propyl]amino]-1,4-dihydro-1,4-dioxo-, 2-naphthalenecarbonitrile, 8-amino-1,4-dihydro-1,4-dioxo-5-(phenylamino)-3-[[3-(triethoxysilyl)propyl]amino]-, 1H-naphth[2,3-f]isoindole-1,3,5,10(2H)-tetrone, 4,11-diamino-2-[3-(triethoxysilyl)propyl]-, 2-naphthalenecarbonitrile, 8-amino-1,4-dihydro-1,4-dioxo-3-[[3-(triethoxysilyl)propyl]amino]-, and dibenzo[a,c]phenazinium, 9-phenyl-11-[[3-(triethoxysilyl)propyl]amino]-, chloride.

The compounds of formula (I) may also be chosen from:

benzamide, N-[3-(dimethoxymethylsilyl)propyl]-4-[(8-hydroxy-5-quinolinyl)azo], benzenamine, N-[3-(diethoxymethylsilyl)propyl]-N-methyl-4-[(4-nitrophenyl)azo, 2-propenoate of 2-methyl-, 3-[bis[2-[ethyl[4-[(4-nitrophenyl)azo]phenyl]amino]ethoxy]methylsilyl]propyl ester, benzamide, N-cyclohexyl-3-[(2,2-dicyanoethyl)azo]-N-[3-(dimethoxymethylsilyl)propyl], 2-propenoate of 2-methyl-, 2-[ethyl[4-[(4-nitrophenyl)azo]phenyl]amino]ethyl ester, 2-[2-[[(2-bicyclo[4,2,0]octa-1,3,5-trien-3-ylethenyl)oxy][(2-bicyclo[4,2,0]oct-3-ylethenyl)oxy]methylsilyl]ethyl]-N,N-dimethyl-4-[(4-nitrophenyl)azo], hexanamide, N-[3-(diethoxymethylsilyl)propyl]-6-[4-[(4-hexylphenyl)azo]phenoxy], and hexanamide, N-[3-(diethoxymethylsilyl)propyl]-6-[4-[(4-hexylphenyl)azo]phenoxy.

The composition according to the present disclosure may comprise from 0.001 to 20%, for example, from 0.01 to 10%, or from 0.1 to 5% by weight of the at least one direct dye of formula (I) relative to the total weight of the composition.

The dyes of the present disclosure may be prepared according to chemical reactions known in the art, from functionalized chromophores capable of reacting with the chosen linking arm. The dyes may be prepared, for example, by the method described in French Patent No. 2 421 934.

Additional Direct Dyes

The dye composition in accordance with the present disclosure may also contain at least one additional direct dye other than the direct dyes of formula (I) described above, which may be chosen from the abovementioned direct dyes, for example, from neutral, acidic, and cationic nitro dyes of the benzene series; neutral, acidic, and cationic azo direct dyes; neutral, acidic, and cationic quinone direct dyes, such as anthraquinone direct dyes; azine direct dyes; triarylmethane direct dyes; indoamine direct dyes; and natural direct dyes.

The at least one additional direct dye may be present in the composition in an amount ranging from 0.001 to 20% by weight of the total weight of the ready-to-use composition, for example, from 0.005 to 10% by weight.

Oxidation Dye Precursors

The compositions of the present disclosure may also comprise at least one oxidation dye precursor, for example, oxidation bases.

Examples of suitable oxidation bases in accordance with the present disclosure include, but are not limited to, phenylenediamines, bisphenylalkylenediamines, para-aminophenols, ortho-aminophenols, heterocyclic bases other than the heterocyclic para-phenylenediamines of formula (I), and their addition salts.

Non-limiting examples of para-phenylenediamines include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-α-hydroxyethylamino-5-aminotoluene, 3-hydroxy-1-(4'-aminophenyl)pyrrolidine, and their acid addition salts.

In one embodiment, the para-phenylenediamines may be chosen from para-phenylenediamine, para-tolylenediamine, 2-isopropyl-para-phenylenediamine, 2-β-hydroxyethyl-para-phenylenediamine, 2-α-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their acid addition salts.

Examples of bisphenylalkylenediamines include, but are not limited to, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their addition salts.

Non-limiting examples of para-aminophenols include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their acid addition salts.

Suitable ortho-aminophenols may be chosen from, for example, 2-aminophenol, 2-amino-5-methylphenol, 2-amino-6-methylphenol, 5-acetamido-2-aminophenol, and their addition salts.

Examples of heterocyclic bases include, but are not limited to, pyridine derivatives, pyrimidine derivatives, and pyrazole derivatives.

Pyridine derivatives may be chosen from the compounds described, for example, in British Patent Nos. GB 1,026,978 and GB 1,153,196, and 2,5-diaminopyridine, 2-(4-methoxyphenyl)amino-3-aminopyridine, 3,4-diaminopyridine, and their addition salts.

Other pyridine oxidation bases useful in the present disclosure include, but are not limited to, the oxidation bases 3-aminopyrazolo[1,5-a]pyridines and their addition salts which are described, for example, in French Patent Application No. FR 2 801 308. Non-limiting examples of such pyridine oxidation bases include pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamino; (3-aminopyrazolo[1,5-a]pyridin-7-yl)methanol; 2-(3-aminopyrazolo[1,5-a]pyridin-5-yl)methanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazol[1,5-a]pyridin-5-yl)-(2-hydroxyethyl)amino]ethanol; 2-[(3-aminopyrazolo[1,5-a]pyridin-7-yl)(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and their addition salts.

Suitable pyrimidine derivatives include, for example, the compounds described in German Patent No. DE 23 59 399; Japanese Patent Nos. JP 88-169571 and JP 05-163124; European Patent No. EP 0 770 375, and International Publication No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, their addition salts, and their tautomeric forms, when a tautomeric equilibrium exists.

Non-limiting examples of pyrazole derivatives include the compounds described in German Patent Nos. DE 38 43 892, 41 33 957, and 195 43 988, International Publication Nos. WO 94/08969 and WO 94/08970, and French Patent No. FR 2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts.

The at least one oxidation base may each be present in the composition of the present disclosure in an amount ranging from 0.001 to 20% by weight of the total weight of the dye composition, for example, from 0.005 to 6%.

The composition of the present disclosure may additionally comprise at least one oxidation dye coupler.

The at least one coupler may be chosen from couplers conventionally used for dyeing keratin fibers, for example, meta-phenylenediamines, meta-diphenols, naphthalene couplers, heterocyclic couplers, and their addition salts.

Non-limiting examples of couplers include 1,3-dihydroxybenzene, 1,3-dihydroxy-2-methylbenzene, 4-chloro-1, 3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and their addition salts.

The at least one coupler may be present in the composition of the present disclosure in an amount ranging from 0.001 to 20% by weight of the total weight of the dye composition, for example, from 0.005 to 6%.

In general, the addition salts of the oxidation bases and couplers which may be used in accordance with the present disclosure include, for example, the acid addition salts such as the hydrochlorides, hydrobromides, sulphates, citrates, succinates, tartrates, lactates, tosylates, benzenesulphonates, phosphates, and acetates, and the base addition salts such as sodium hydroxide, potassium hydroxide, ammonium hydroxide, amines, and alkanolamines.

Medium Appropriate for Dyeing

The medium appropriate for dyeing, also called dye carrier, is a cosmetic medium generally comprising water or a mixture of water and/or at least one organic solvent for solubilizing the compounds which might not be sufficiently soluble in water. Suitable organic solvents include, for example, lower $C_1$-$C_4$ alkanols, such as ethanol and isopropanol; polyols and polyol ethers such as 2-butoxyethanol, propylene glycol, propylene glycol monomethyl ether, diethylene glycol monoethyl ether, and monomethyl ether; aromatic alcohols such as benzyl alcohol and phenoxyethanol, and mixtures thereof.

The at least one solvent may be present in an amount ranging from 1 to 99% by weight relative to the total weight of the dye composition, for example, from 10 to 95% by weight.

Adjuvants

The dye composition in accordance with the present disclosure may also contain at least one adjuvant chosen from various adjuvants conventionally used in hair dye compositions, such as anionic, cationic, nonionic, amphoteric, and zwitterionic surfactants and mixtures thereof; anionic, cationic, nonionic, amphoteric, and zwitterionic polymers and mixtures thereof, inorganic and organic thickeners, for example, associative thickeners such as anionic, cationic, nonionic, and amphoteric polymers; antioxidants; penetrating agents; sequestrants; perfumes; buffers; dispersing agents; conditioning agents such as modified or unmodified, volatile or nonvolatile silicones; film-forming agents; ceramides; preservatives; and opacifying agents.

The at least one adjuvant may be present in an amount (each) ranging from 0.01 to 20% by weight relative to the total weight of the dye composition.

Of course, persons skilled in the art will be careful to choose this or these optional additional compounds such that the advantageous properties intrinsically attached to the oxidation dye composition in accordance with the present disclosure are not, or not substantially, impaired by the addition envisaged.

The pH of the dye composition in accordance with the present disclosure may range generally from 3 to 12, for example, from 5 to 11. The pH may be adjusted to the desired value by means of acidifying or alkalinizing agents customarily used in dyeing keratin fibers or with the aid of conventional buffering systems.

Examples of suitable acidifying agents include, but are not limited to, inorganic and organic acids such as hydrochloric acid, orthophosphoric acid, sulphuric acid, carboxylic acids such as acetic acid, tartaric acid, citric acid, lactic acid, and sulphonic acids.

Non-limiting examples of alkalinizing agents include ammonium hydroxide, alkali metal carbonates, alkanolamines such as mono-, di-, and triethanolamines and derivatives thereof, sodium hydroxides, potassium hydroxides, and compounds of formula (III):

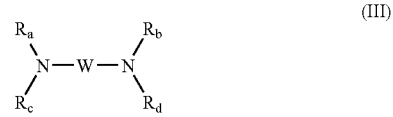

in which
  W is a propylene residue optionally substituted with an entity chosen from hydroxyl groups and $C_1$-$C_4$ alkyl radicals; and
  $R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

The dye composition according to the present disclosure may be provided in various forms, chosen, for example, from liquids, creams, and gels, and any other appropriate form for dyeing keratin fibers such as human hair.

Dyeing Methods

At least one method according to the present disclosure may comprise applying a dye composition according to the present disclosure to the keratin fibers, and leaving the dye composition in for a sufficient period to allow for dyeing of the hair. This period generally ranges from 5 minutes to 1 hour, for example, from 15 minutes to 1 hour. In one embodiment, this direct dyeing may be performed in the presence of an oxidizing agent.

Another method for dyeing keratin fibers may comprise applying to the keratin fibers a first composition comprising at least one compound of formula (I), leaving the first composition in for a period ranging from 5 minutes to one hour, and then, after an optional rinse, applying to the keratin fibers a second composition comprising at least one alkaline agent as defined above, with a leave-in time ranging from a few seconds to 30 minutes.

When the composition according to the present disclosure comprises at least one oxidation dye precursor, the method for dyeing keratin fibers may further comprise developing the color with the aid of an oxidizing agent. The color may be developed at an acidic, neutral, or alkaline pH and the oxidizing agent may be added to the composition of the present disclosure just at the time of use or it may be used from an oxidizing composition containing it, applied simultaneously with or sequentially to the composition of the present disclosure.

The method may thus comprise applying a first composition according to the present disclosure comprising at least one oxidation dye precursor and at least one organosilane compound of formula (I), and leaving the first composition in for a period ranging from 5 to 60 minutes, and then, after an optional rinse, applying a second composition comprising at least one oxidizing agent and at least one alkaline agent, which is left in for a period ranging from 5 minutes to 60 minutes.

According to one embodiment, a first composition according to the present disclosure comprising at least one compound of formula (I) and at least one oxidation dye precursor, is mixed, for example, at the time of use, with a second composition comprising, in a medium appropriate for dyeing, at least one oxidizing agent, this oxidizing agent being present in an amount sufficient to develop a color. The mixture thus obtained is then applied to the keratin fibers. After a leave-in time ranging from 5 minutes to 1 hour, for example, from 15 minutes to 1 hour, the keratin fibers are rinsed, optionally washed with shampoo and then rinsed again, and dried.

According to another embodiment, a first composition comprising at least one compound of formula (I) and an oxidation dye precursor is applied to the keratin fibers, and then, after a leave-in time ranging from 5 to 60 min and after an optional rinse, a second composition comprising at least one oxidizing agent and at least one alkaline agent is applied. After another leave-in time ranging from 5 minutes to one hour, for example, from 15 minutes to one hour, the keratin fibers are rinsed, optionally washed with shampoo and then rinsed again, and then dried.

The oxidizing agents conventionally used for the oxidation dyeing of keratin fibers include, for example, hydrogen peroxide, urea peroxide, alkali metal bromates, persalts such as perborates and persulphates, peracids, and the oxidase enzymes, for example, peroxidases, oxidoreductases with 2 electrons such as uricases, and oxygenases with 4 electrons such as laccases. In at least one embodiment, the oxidizing agent may be hydrogen peroxide.

The oxidizing composition may also contain various adjuvants conventionally used in hair dye compositions and as defined above.

The pH of the oxidizing composition comprising the oxidizing agent is such that, after mixing with the dye composition, the pH of the resulting composition applied to the keratin fibers ranges from 3 to 12, for example, from 5 to 11, or from 6 to 10.5. The pH may be adjusted to the desired value by means of pH-regulating, acidifying or alkalinizing agents customarily used for dyeing keratin fibers and as defined above.

The composition applied to the keratin fibers may be provided in various forms, chosen, for example, from liquids, creams, gels, and any other form appropriate for dyeing keratin fibers such as human hair. In one embodiment, the composition may be packaged under pressure in an aerosol can in the presence of a propellant and form a foam.

Also disclosed herein is a multicompartment device or dye "kit" in which a first compartment contains the dye composition defined herein and a second compartment contains an oxidizing composition. This device may be equipped with means which make it possible to deliver the desired mixture to the hair, such as the devices described in French Patent No. 2 586 913.

Using this device, it is possible to dye the keratin fibers using a method which comprises mixing a dye composition in accordance with the present disclosure with an oxidizing agent as defined above, and applying the mixture obtained to the keratin fibers for a time sufficient to develop the desired color.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLE

Three compositions were prepared in accordance with the present disclosure:

|  | Composition A | Composition B |
|---|---|---|
| Ethanol | 89 g | — |
| Water | 10 g | 97 g |
| Monoethanolamine | — | 3 g |
| Dye | 1 g | — |

Composition A was prepared for two separate trials, using two separate dyes having a trialkoxysilane functional group:
3-(2,4-dinitrophenylamino)propyltriethoxysilane (compound of formula X), and
N-(triethoxysilylpropyl)dansylamide (compound of formula Y)

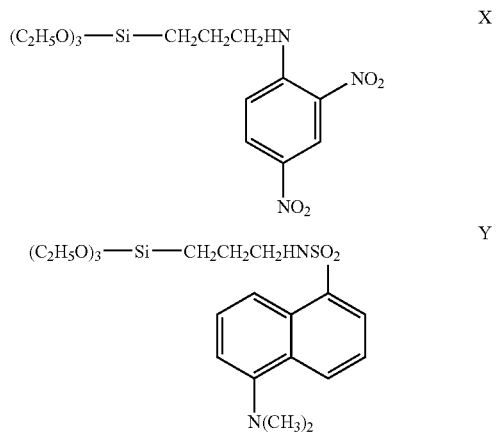

In each trial, Composition A was applied to locks (1 g each) of natural grey hair and permanently waved grey hair with a bath ratio equivalent to 10 g of composition A per 1 g of hair. After leaving in for 30 minutes, Composition B was applied (bath ratio of 5 g of composition B per 1 g of hair). After leaving in for 15 minutes, the locks were rinsed and washed with shampoo, and then dried. During the entire leave-in time, the locks were placed at 45° C.

Results

The glint obtained when the composition A comprises the dye X is an intense golden. The color is fast to repeated washing.

When the composition A comprises the dye Y, the color obtained is an intense yellow which is very fast to repeated washing.

What is claimed is:

1. A method for the direct dyeing of keratin fibers, comprising applying to the keratin fibers a dye composition comprising at least one organosilane compound chosen from compounds of formula (I):

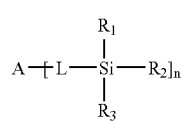

in which:
A is a group having a direct dyeing function,
L is a linking arm,
$R_1$, $R_2$, and $R_3$, independently of each other, are chosen from hydrogen; mono- and polyhydroxyalkyl radicals comprising from 1 to 10 carbon atoms; mono- and polyaminoalkyl radicals comprising from 1 to 10 carbon atoms; mono- and polyhaloalkyl radicals comprising from 1 to 10 carbon atoms; mono- and polyalkoxyalkyl radicals, wherein the alkoxy radicals are chosen from $C_1$-$C_{10}$ alkoxy radicals and the alkyl radicals are chosen from $C_1$-$C_{10}$ alkyl radicals; $C_6$-$C_{18}$ aryl radicals; $C_6$-$C_{18}$ mono- and polyaminoaryl radicals; $C_6$-$C_{18}$ mono- and polyhydroxyaryl radicals; mono- and polyalkoxyaryl radicals, wherein the alkoxy radical is chosen from $C_1$-$C_{10}$ alkoxy radicals and the aryl radical is chosen from $C_6$-$C_{18}$ aryl radicals; alkylaryl radicals, wherein the alkyl radical is chosen from $C_1$-$C_{10}$ alkyl radicals and the aryl radical is chosen from $C_6$-$C_{18}$ aryl radicals; arylalkyl radicals, wherein the alkyl radical is chosen from $C_1$-$C_{10}$ alkyl radicals and the aryl radical is chosen from $C_6$-$C_{18}$ aryl radicals; carboxyalkyl and sulphoalkyl radicals, wherein the alkyl radical is chosen from $C_1$-$C_{10}$ alkyl radicals; and
n is an integer ranging from 1 to 10.

2. The method of claim 1, wherein the keratin fibers are human hair.

3. The method of claim 1, wherein the at least one organosilane compound is chosen from compounds of formula (II):

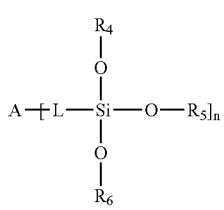

in which:
A is a group having a direct dyeing function,
L is a linking arm,
$R_4$, $R_5$, and $R_6$, independently of each other, are chosen from linear or branched, $C_1$-$C_{10}$ alkyl radicals, and
n is an integer ranging from 1 to 10.

4. The method of claim 3, wherein the alkyl radicals of $R_4$, $R_5$, and $R_6$ are chosen from $C_1$-$C_6$ alkyl radicals.

5. The method of claim 1, wherein A is chosen from radicals derived from aromatic nitro, anthraquinone, naphthoquinone, benzoquinone, azo, xanthene, triarylmethane, azine, thiazine, phenothiazine, diazine, phenodiazine, acridine, cyaninemethine, azomethine, nitro, phthalocyanine, and indoaniline dyes, and natural direct dyes.

6. The method of claim 1, wherein the linking arm L is chosen from linear or branched, $C_1$-$C_{20}$ hydrocarbon chains, wherein at least one carbon atom of the chain may optionally be replaced by a heteroatom, and wherein the chain may be saturated or unsaturated and/or may comprise at least one radical chosen from arylene; divalent terephthalamide; divalent triazine; and —NHCO— radicals.

7. The method of claim 6, wherein the hydrocarbon chain L is substituted with at least one radical chosen from hydroxyl, alkoxy, amino, alkylamino, and halogen radicals.

8. The method of claim 6, wherein the linking arm L is chosen from linear or branched $C_1$-$C_{20}$ alkylene chains.

9. A method for making a dye composition for the direct dyeing of keratin fibers, comprising including in said composition, in an appropriate dyeing medium, at least one organosilane compound chosen from compounds of formula (I):

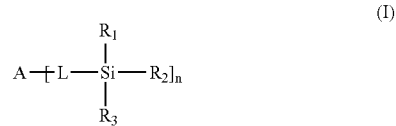

in which:
A is a group having a direct dyeing function,
L is a linking arm,
$R_1$, $R_2$, and $R_3$, independently of each other, are chosen from hydrogen; mono- and polyhydroxyalkyl radicals comprising from 1 to 10 carbon atoms; mono- and polyaminoalkyl radicals comprising from 1 to 10 carbon atoms; mono- and polyhaloalkyl radicals comprising from 1 to 10 carbon atoms; mono- and polyalkoxyalkyl radicals, wherein the alkoxy radicals are chosen from $C_1$-$C_{10}$ alkoxy radicals and the alkyl radicals are chosen from $C_1$-$C_{10}$ alkyl radicals; $C_6$-$C_{18}$ aryl radicals; $C_6$-$C_{18}$ mono- and polyaminoaryl radicals; $C_6$-$C_{18}$ mono- and polyhydroxyaryl radicals; mono- and polyalkoxyaryl radicals, wherein the alkoxy radical is chosen from $C_1$-$C_{10}$ alkoxy radicals and the aryl radical is chosen from $C_6$-$C_{18}$ aryl radicals; alkylaryl radicals, wherein the alkyl radical is chosen from $C_1$-$C_{10}$ alkyl radicals and the aryl radical is chosen from $C_6$-$C_{18}$ aryl radicals; arylalkyl radicals, wherein the alkyl radical is chosen from $C_1$-$C_{10}$ alkyl radicals and the aryl radical is chosen from $C_6$-$C_{18}$ aryl radicals; carboxyalkyl and sulphoalkyl radicals, wherein the alkyl radical is chosen from $C_1$-$C_{10}$ alkyl radicals; and
n is an integer ranging from 1 to 10.

10. A dye composition for dyeing keratin fibers, comprising, in an appropriate dyeing medium, at least one oxidation base and at least one organosilane compound chosen from compounds of formula (I):

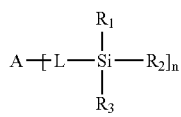

in which:
A is a group having a direct dyeing function,
L is a linking arm,
$R_1$, $R_2$, and $R_3$, independently of each other, are chosen from hydrogen; mono- and polyhydroxyalkyl radicals comprising from 1 to 10 carbon atoms; mono- and polyaminoalkyl radicals comprising from 1 to 10 carbon atoms; mono- and polyhaloalkyl radicals comprising from 1 to 10 carbon atoms; mono- and polyalkoxyalkyl radicals, wherein the alkoxy radical is chosen from $C_1$-$C_{10}$ alkoxy radicals and the alkyl radical is chosen from $C_1$-$C_{10}$ alkyl radicals; $C_6$-$C_{18}$ aryl radicals; $C_6$-$C_{18}$ mono- and polyaminoaryl radicals; $C_6$-$C_{18}$ mono- and polyhydroxyaryl radicals; mono- and polyalkoxyaryl radicals, wherein the alkoxy radical is chosen from $C_1$-$C_{10}$ alkoxy radicals and the aryl radical is chosen from $C_6$-$C_{18}$ ayl radicals; alkylaryl radicals, wherein the alkyl radical is chosen from $C_1$-$C_{10}$ alkyl radicals and the aryl radical is chosen from $C_6$-$C_{18}$ aryl radicals; arylalkyl radicals, wherein the alkyl radical is chosen from $C_1$-$C_{10}$ alkyl radicals and the aryl radical is chosen from $C_6$-$C_{18}$ aryl radicals; carboxyalkyl and sulphoalkyl radicals, wherein the alkyl radical is chosen from $C_1$-$C_{10}$ alkyl radicals; and
n is an integer ranging from 1 to 10.

11. The composition of claim 10, wherein the keratin fibers are human hair.

12. The composition of claim 10, wherein the at least one organosilane compound is chosen from compounds of formula (II):

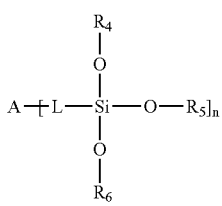

in which:
A is a group having a direct dyeing function,
L is a linking arm,
$R_4$, $R_5$ and $R_6$, independently of each other, are chosen from linear or branched, $C_1$-$C_{10}$ alkyl radicals, and
n is an integer ranging from 1 to 10.

13. The composition of claim 10, wherein A is chosen from radicals derived from aromatic nitro, anthraquinone, naphthoquinone, benzoquinone, azo, xanthene, triarylmethane, azine, thiazine, phenothiazine, diazine, phenodiazine, acridine, cyaninemethine, azomethine, nitro, phthalocyanine, and indoaniline dyes, and natural direct dyes.

14. The composition of claim 10, wherein the linking arm L is chosen from linear or branched, $C_1$-$C_{20}$ hydrocarbon chains, wherein at least one carbon atom of the chain may optionally be replaced by a heteroatom, and wherein the chain may be saturated or unsaturated and/or may comprise at least one radical chosen from arylene; divalent terephthalamide; divalent triazine; and —NHCO— radicals.

15. The composition of claim 14, wherein the hydrocarbon chain L is substituted with at least one radical chosen from hydroxyl, alkoxy, amino, alkylamino, and halogen radicals.

16. The composition of claim 14, wherein the linking arm L is chosen from linear or branched $C_1$-$C_{20}$ alkylene chains.

17. The composition of claim 10, wherein the at least one direct dye of formula (I) is present in the composition in an amount ranging from 0.001 to 20% by weight relative to the total weight of the composition.

18. The composition of claim 17, wherein the at least one direct dye of formula (I) is present in the composition in an amount ranging from 0.1 to 5% by weight relative to the total weight of the composition.

19. The composition of claim 10, wherein the at least one oxidation base is chosen from para-phenylenediamines, bisphenylalkylenediamines, para-aminophenols, ortho-aminophenols, heterocyclic bases, and the addition salts thereof.

20. The composition of claim 10, wherein the at least one oxidation base is present in the composition in an amount, for each oxidation base, ranging from 0.001 to 20% by weight relative to the total weight of the composition.

21. The composition of claim 20, wherein the at least one oxidation base is present in the composition in an amount ranging from 0.005 to 6% by weight relative to the total weight of the composition.

22. The composition of claim 10, further comprising at least one oxidation coupler.

23. The composition of claim 22, wherein the at least one coupler is chosen from meta-phenylenediamines, meta-aminophenols, meta-diphenols, naphthalene couplers, heterocyclic couplers, and the addition salts thereof.

24. The composition of claim 23, wherein the at least one coupler is chosen from 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, and the addition salts thereof.

25. The composition of claim 22, wherein the at least one coupler is present in an amount ranging from 0.001 to 20% by weight relative to the total weight of the composition.

26. The composition of claim 25, wherein the at least one coupler is present in an amount ranging from 0.005 to 6% by weight relative to the total weight of the composition.

27. The composition of claim 10, further comprising at least one additional direct dye.

28. The composition of claim 10, further comprising at least one organic solvent.

29. The composition of claim 28, wherein the at least one organic solvent is chosen from ethanol, propylene glycol, glycerol, and polyol monoethers.

30. The composition of claim 10, further comprising at least one adjuvant chosen from anionic, cationic, nonionic, amphoteric, and zwitterionic surfactants and mixtures thereof; anionic, cationic, nonionic, amphoteric, and zwitterionic polymers and mixtures thereof; inorganic and organic thickeners; antioxidants; penetrating agents; sequestrants; perfumes; buffers; dispersing agents; conditioning agents; film-forming agents; ceramides; preservatives; and opacifying agents.

31. The composition of claim 10, further comprising at least one oxidizing agent chosen from hydrogen peroxide, urea peroxide, alkali metal bromates, persalts, peracids, and oxidase enzymes.

32. The composition of claim 31, wherein the at least one oxidizing agent is hydrogen peroxide.

33. A method for dyeing keratin fibers comprising applying to said fibers a first composition, and leaving the first composition in the keratin fibers for a time period ranging from 5 minutes to one hour;
wherein the first composition comprises, in an appropriate dyeing medium, at least one oxidation base and at least one organosilane compound chosen from compounds of formula (I):

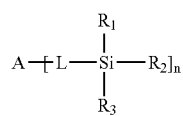

(I)

in which:
A is a group having a direct dyeing function,
L is a linking arm,
$R_1$, $R_2$, and $R_3$, independently of each other, are chosen from hydrogen; mono- and polyhydroxyalkyl radicals comprising from 1 to 10 carbon atoms; mono- and polyaminoalkyl radicals comprising from 1 to 10 carbon atoms; mono- and polyhaloalkyl radicals comprising from 1 to 10 carbon atoms; mono- and polyalkoxyalkyl radicals, wherein the alkoxy radical is chosen from $C_1$-$C_{10}$ alkoxy radicals and the alkyl radical is chosen from $C_1$-$C_{10}$ alkyl radicals; $C_6$-$C_{18}$ aryl radicals; $C_6$-$C_{18}$ mono- and polyaminoaryl radicals; $C_6$-$C_{18}$ mono- and polyhydroxyaryl radicals; mono- and polyalkoxyaryl radicals, wherein the alkoxy radical is chosen from $C_1$-$C_{10}$ alkoxy radicals and the aryl radical is chosen from $C_6$-$C_{18}$ ayl radicals; alkylaryl radicals, wherein the alkyl radical is chosen from $C_1$-$C_{10}$ alkyl radicals and the aryl radical is chosen from $C_6$-$C_{18}$ aryl radicals; arylalkyl radicals, wherein the alkyl radical is chosen from $C_1$-$C_{10}$ alkyl radicals and the aryl radical is chosen from $C_6$-$C_{18}$ aryl radicals; carboxyalkyl and sulphoalkyl radicals, wherein the alkyl radical is chosen from $C_1$-$C_{10}$ alkyl radicals; and
n is an integer ranging from 1 to 10.

34. The method of claim 33, wherein the time period ranges from 15 minutes to 1 hour.

35. The method of claim 33, further comprising optionally rinsing the first composition from the keratin fibers and applying a second composition comprising at least one alkaline agent for a leave-in time ranging from a few seconds to 30 minutes.

36. The method of claim 33, further comprising optionally rinsing the first composition from the keratin fibers and applying a second composition comprising at least one oxidizing agent and at least one alkaline agent, which is left in for 5 minutes to 60 minutes.

37. The method of claim 33, wherein the keratin fibers are human hair.

38. A method for providing keratin fibers with a color having good resistance to external agents and shampoos, comprising applying to said keratin fibers a dye composition comprising, in an appropriate dyeing medium, at least one oxidation base and at least one organosilane compound chosen from compounds of formula (I):

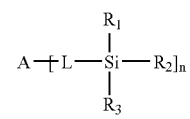

(I)

in which:
A is a group having a direct dyeing function,
L is a linking arm,
$R_1$, $R_2$, and $R_3$, independently of each other, are chosen from hydrogen; mono- and polyhydroxyalkyl radicals comprising from 1 to 10 carbon atoms; mono- and polyaminoalkyl radicals comprising from 1 to 10 carbon atoms; mono- and polyhaloalkyl radicals comprising from 1 to 10 carbon atoms; mono- and polyalkoxyalkyl radicals, wherein the alkoxy radical is chosen from $C_1$-$C_{10}$ alkoxy radicals and the alkyl radical is chosen from $C_1$-$C_{10}$ alkyl radicals; $C_6$-$C_{18}$ aryl radicals; $C_6$-$C_{18}$ mono- and polyaminoaryl radicals; $C_6$-$C_{18}$ mono- and polyhydroxyaryl radicals; mono- and polyalkoxyaryl radicals, wherein the alkoxy radical is chosen from $C_1$-$C_{10}$ alkoxy radicals and the aryl radical is chosen from $C_6$-$C_{18}$ ayl radicals; alkylaryl radicals, wherein the alkyl radical is chosen from $C_1$-$C_{10}$ alkyl radicals and the aryl radical is chosen from $C_6$-$C_{18}$ aryl radicals; arylalkyl radicals, wherein the alkyl radical is chosen from $C_1$-$C_{10}$ alkyl radicals and the aryl radical is chosen from $C_6$-$C_{18}$ aryl radicals; carboxyalkyl and sulphoalkyl radicals, wherein the alkyl radical is chosen from $C_1$-$C_{10}$ alkyl radicals; and
n is an integer ranging from 1 to 10.

* * * * *